US012602756B2

(12) United States Patent
Andrew

(10) Patent No.: US 12,602,756 B2
(45) Date of Patent: Apr. 14, 2026

(54) METHOD AND SYSTEM FOR ANALYTICAL X-RAY CALIBRATION, RECONSTRUCTION AND INDEXING USING SIMULATION

(71) Applicant: Carl Zeiss X-ray Microscopy, Inc., Dublin, CA (US)

(72) Inventor: Matthew Andrew, Livermore, CA (US)

(73) Assignee: Carl Zeiss X-ray Microscopy, Inc., Dublin, CA (US)

( * ) Notice: Subject to any disclaimer, the term of this patent is extended or adjusted under 35 U.S.C. 154(b) by 722 days.

(21) Appl. No.: 18/048,178

(22) Filed: Oct. 20, 2022

(65) Prior Publication Data

US 2023/0143112 A1 May 11, 2023

Related U.S. Application Data

(60) Provisional application No. 63/263,626, filed on Nov. 5, 2021.

(51) Int. Cl.
    *G06F 30/20*     (2020.01)
    *G01N 23/046*     (2018.01)
    (Continued)

(52) U.S. Cl.
    CPC ............. *G06T 7/00* (2013.01); *G01N 23/046* (2013.01); *G01N 23/083* (2013.01); *G01N 33/24* (2013.01);
    (Continued)

(58) Field of Classification Search
    CPC ...... G06T 7/00; G01N 23/046; G01N 23/083; G01N 33/24; G01N 2223/04;
    (Continued)

(56) References Cited

U.S. PATENT DOCUMENTS

| | | | |
|---|---|---|---|
| 2017/0228897 A1 | 8/2017 | Holt et al. | |
| 2018/0082447 A1* | 3/2018 | Recur ...................... | G06T 7/11 |

(Continued)

OTHER PUBLICATIONS

European Search Report, completed on Feb. 28, 2023, from European Application No. EP 22204837.3, filed on Jan. 18, 2023. 8 pages.

(Continued)

*Primary Examiner* — Juan M Guillermety
(74) *Attorney, Agent, or Firm* — HoustonHogle LLP

(57) ABSTRACT

A mineral characterization method for an x-ray CT system comprises generating one or more volume datasets of a sample and identifying phases in the sample by correcting the datasets based on simulations. This can be employed with a polychromatic x-ray simulation and a highly controlled and well scaled implementation of analytical reconstruction to index materials of known composition to reconstructed grayscale intensities. An example of an application of this technology is in the field of mineral characterization on geoscience samples, where a single sample may consist of many individual mineral phases, of unknown distribution. Also addressed is a workflow for data correction and calibration such that acquisition related uncertainties are minimized and reconstructed intensity robustness maximized. This is achieved when some material of known transmission is in the field of view for every projection to create a reference path.

18 Claims, 10 Drawing Sheets

(51) Int. Cl.
    *G01N 23/083*     (2018.01)
    *G01N 33/24*     (2006.01)
    *G06T 7/00*     (2017.01)

(52) U.S. Cl.
    CPC ......... *G06F 30/20* (2020.01); *G01N 2223/04*
        (2013.01); *G01N 2223/3306* (2013.01); *G01N*
            *2223/419* (2013.01); *G01N 2223/616*
                                  (2013.01)

(58) Field of Classification Search
    CPC ..... G01N 2223/3306; G01N 2223/419; G01N
                2223/616; G06F 30/20; G16C 60/00
    See application file for complete search history.

(56) References Cited

U.S. PATENT DOCUMENTS

| | | | |
|---|---|---|---|
| 2018/0121579 A1* | 5/2018 | Fredrich | .................. G06T 7/11 |
| 2021/0065924 A1* | 3/2021 | Dey | .................... G01N 23/041 |
| 2022/0092768 A1* | 3/2022 | Melapudi | .............. A61B 6/482 |
| 2023/0127194 A1* | 4/2023 | Pichumani | .......... G01N 23/046 |
| | | | 382/149 |

OTHER PUBLICATIONS

Jones et al., "Assessment of bone ingrowth into porous biomaterials using MICRO-CT, Imaging Tech. Biomater. Charact.", 28(15), 2491-2504), 2007, 14 Pages.

\* cited by examiner

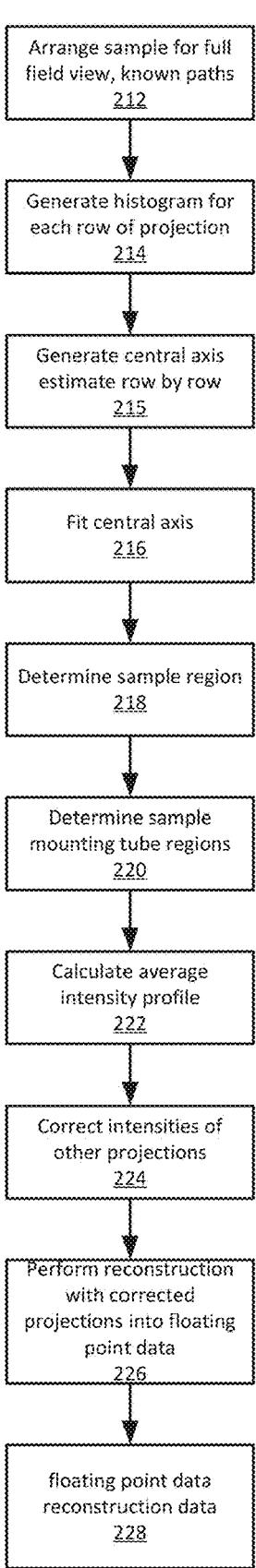

Arrange sample for full
field view, known paths
212

Generate histogram for
each row of projection
214

Generate central axis
estimate row by row
215

Fit central axis
216

Determine sample region
218

Determine sample
mounting tube regions
220

Calculate average
intensity profile
222

Correct intensities of
other projections
224

Perform reconstruction
with corrected
projections into floating
point data
226 floating point data
reconstruction data
228

Fig. 2

METHOD AND SYSTEM FOR ANALYTICAL X-RAY CALIBRATION, RECONSTRUCTION AND INDEXING USING SIMULATION

RELATED APPLICATIONS

This application claims the benefit under 35 USC 119(e) of U.S. Provisional Application No. 63/263,626, filed on Nov. 5, 2021, which is incorporated herein by reference in its entirety.

BACKGROUND OF THE INVENTION

Various imaging modalities have been used to identify and visualize the mineral content and distribution in rocks, both in two dimensions (2D) and in three dimensions (3D). For example, these imaging modalities can analyze rock samples from extraction operations to determine porosity and mineralogy for exploration and production operations in the Oil and Gas industry, or determine comminution statistics for the mining industry.

In typical operation, these imaging modalities create image datasets such as 3D volumes or 2D images. Image analysis techniques are then employed to infer grain characteristics and mineral content from the volumes and the images.

Non-destructive imaging systems include x-ray computed tomography (CT) microscopy and Scanning Electron Microscopy (SEM) systems. These systems provide the ability to visualize features such as pores, organics and minerals in the samples.

The X-ray CT microscopy systems irradiate the sample with x-rays, typically in a range between 1 and several hundred keV. 2D projection images are collected at multiple angles and a 3D volume of the sample is reconstructed from the projections. While the CT intensity correlates with mineral density, there is no direct way of identifying mineralogy on an X-ray CT microscope system, without a prior knowledge.

One current imaging analysis technique creates a 3D mineral map of the sample by analyzing volume image datasets of a sample created from x-ray imaging systems. A total mineral content of the sample is then defined, and x-ray attenuation coefficients are calculated for the defined minerals. The technique then segments the grey scale 3D images by identifying characteristic grey scale levels in the images corresponding to the calculated x-ray attenuation coefficients.

Another imaging analysis technique employs multi-phase segmentation of 3D x-ray tomography volume image datasets. The 3D x-ray tomography volumes are processed to obtain standardized intensity grey scale images, which are then segmented into at least 3 phases. The segmentation steps include computing a median/mean-filtered-gradient image of the standardized intensity image, creating an intensity vs. gradient graph from the median/mean-filtered-gradient image and the standardized intensity image, partitioning the intensity vs. gradient graph into regions, and using thresholds defining the regions to segment the standardized grey scale image to create the segmented image. Then, volumetric fractions and spatial distributions of the segmented phases are calculated and compared with target values.

SUMMARY OF THE INVENTION

Current imaging and material, such as mineral, assignment techniques have limitations. The determination of material or mineral identity in an unknown composition and distribution in 3D using x-ray microscopy is challenging. Analytical reconstruction is not typically a focus in microtomography applications. Medical applications reconstruct to so-called hounsfield units which are often defined using internal standards, but microtomography is much more sensitive. This means that these existing applications are more challenging. On top of this, minerology segmentation has been extremely challenging for a long time because of the high level of noise typical in x-ray reconstruction.

Thus, x-ray microscopy is often used in non-analytical workflows where the constituent materials within a sample are already well known and expected. This is because the translation of measured attenuation to 3D reconstruction is complex and hard to predict, and dependent on a range of factors including target status, selected filter, sample composition, and scintillator/detector response. The problem is made more complex when clusters of grains include minerals that are very close in average atomic number. In addition, the technique can assign the wrong mineralogy to voxels/pixels located on the edges or boundaries of areas within the images.

As a consequence, this invention concerns the development of a protocol and workflow which couples polychromatic x-ray simulation and a highly controlled and well scaled implementation of analytical reconstruction to index materials of known composition to reconstructed grayscale intensities. An example of an application of this technology is in the field of mineral characterization on geoscience samples, where a single sample may consist of many individual mineral phases, of unknown distribution. Also addressed is a computer implemented workflow for data correction and calibration such that acquisition related uncertainties are minimized and reconstructed intensity robustness maximized. This is achieved when some material of known transmission is in the field of view for every projection to create a reference path.

In general, according to one aspect, the invention features a material characterization method for an x-ray CT system. In some implementations, the material is a mineral such as from a mining operation. This method comprises generating one or more volume datasets of a sample and identifying phases in the sample by correcting the datasets based on simulations.

Preferably, the simulations include assessing when materials of known composition, density, and thickness are present within the beam propagation path, and when; they are not to determine a nominal transmission for the materials. The nominal transmission can be converted into an effective reconstructed greyscale value by scaling to give an effective linear attenuation coefficient. Scaling by a beam hardening correction routine is preferably used.

In general, the simulations should include simulating the x-ray propagation through geometry of the sample and/or the response of the x-ray CT system.

In the current example, the projections are corrected before being used for generating the volume datasets, such as in floating point data.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 2 is a flow diagram showing a process for automated segmentation and sample fitting for improved reconstruction;

FIGS. 3A, 3B, and 3C are two dimensional histograms from the same projection data reconstructed and processed using different routines in which, FIG. 3A: raw filtered back projection reconstruction, FIG. 3B: back projection reconstruction filtered using a non-local means denoising filter, and FIG. 3C: data reconstructed using a deep learning-based reconstruction.

DETAILED DESCRIPTION OF THE PREFERRED EMBODIMENTS

Figure 1:
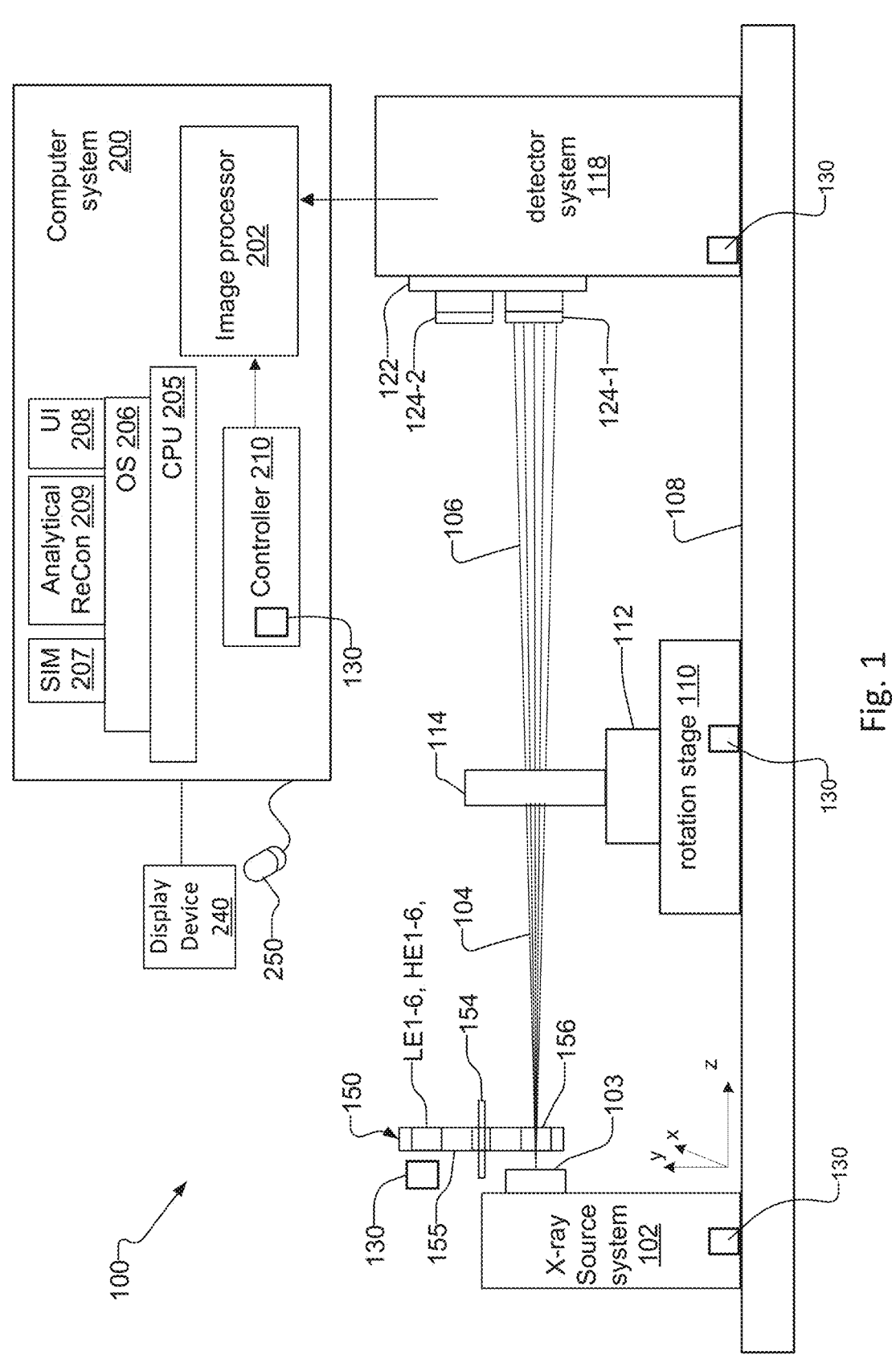
FIG. 1 is a schematic diagram of an x-ray CT system to which the present invention is applicable.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

In general, this invention also concerns the development of a protocol and computer implemented and executed workflow which couples polychromatic x-ray simulation and a highly controlled and well scaled implementation of analytical reconstruction to index materials of known composition to reconstructed grayscale intensities. Also included is a computer implemented and executed workflow for data correction and calibration such that acquisition related uncertainties are minimized and reconstructed intensity robustness maximized.

As a general rule, to get a robust reconstruction, the intensity values of measured x-ray data must be corrected for a variety of sources of spurious signal which are not already corrected for in the x-ray referencing process. This can only be achieved reliably if some material of known transmission is in the field of view for every projection to create a reference path. The simplest arrangement is to have a portion of the projection correspond to a passthrough of only air path. That is, there is a direct line of sight path between the source and the detector in a portion of every projection.

The approach for fulfilling the reference path condition is to perform a "full field of view" tomography and not a region of interest tomography on a specific region of the sample.

Typically, the effective transmission of any air linear integral should be effectively 100%, and any regions of the sample that are common through every projection should have the same linear integral in every projection. The projections can therefore be a scaled search where the transmission/absorption values within these regions are corrected to some nominal value measured on a reference sample. If no common material is available, it is possible to just scale the data sets so the transmission of the average is always 100%.

It should be noted that while theoretically these projection intensities should be the same for every projection, variations in source flux, as well as second-order x-ray effects, such as scatter or secondary unfocused x-rays, can influence the nominal reference attenuation and thereby the reconstructed grayscale value. These are not often corrected for in traditional imaging workflows as they have a very limited impact on overall image quality, and often scientists are not interested in the absolute reconstructed values.

FIG. 1 is a schematic diagram of an x-ray CT system 100 on which the present invention can be implemented.

In general, the x-ray CT system 100 includes an x-ray source system 102 that generates an often polychromatic x-ray beam 104 and a rotation and positioning stage 110 with sample holder 112 for holding the sample 114 in the x-ray beam 104 from the x-ray source system 102. Images or x-ray projections are captured by a detector system 118. The x-ray source system 102, the rotation and positioning stage 110, and the detector system are usually mounted to a base 108 of the x-ray CT system 100.

A computer system 200 typically receives and processes these images or projections and provides general control of the system 100. The computer system 200 possibly along with a special purpose graphics processor will typically perform tomographic reconstruction using the x-ray projections.

The x-ray source 102, in one example, is a polychromatic x-ray source. Laboratory x-ray sources are often used because of their ubiquity and relatively low cost. Nonetheless, synchrotron sources or accelerator-based sources are other alternatives.

Common laboratory x-ray sources include an x-ray tube, in which electrons are accelerated in a vacuum by an electric field and shot into a target piece of metal, with x-rays being emitted as the electrons decelerate in the metal. Typically, such sources produce a continuous spectrum of background x-rays (i.e. bremsstrahlung radiation) combined with sharp peaks in intensity at certain energies that derive from the characteristic lines of the target, depending on the type of metal target used.

In one example, the x-ray source 102 is a rotating anode type or micro focused source, with a Tungsten target. Targets that include Molybdenum, Gold, Platinum, Silver or Copper also can be employed. A transmissive configuration of the x-ray source 102 can be used in which the electron beam strikes the thin target 103 from its backside. The x-rays emitted from the other side of the target 103 are then used as the beam 104. Reflection targets are another option.

The x-ray beam 104 generated by source 102 has an energy spectrum that is controlled typically by the operating parameters of the source. In the case of a laboratory source, important parameters include the material of the target and the acceleration voltage (kVp). The energy spectrum is also dictated by any conditioning filters that suppress unwanted energies or wavelengths of radiation. For example, undesired wavelengths present in the beam can be eliminated or attenuated using, for instance, an energy filter (designed to select a desired x-ray wavelength range/bandwidth).

A filter wheel 150 may include several filters LE1-6 HE1-6 that are placed in the path of the x-ray beam 103 to serve as an energy filter. Operators of current x-ray CT systems will often use the filters to modify and/or compensate for the beam hardening property of the x-ray output.

In more detail, the filter wheel 150 is controlled by the controller 210 of the computer system 200. The filter wheel 150 includes a frame 155 that rotates on axle 154 under control of the controller 210 via its control interface 130. Via the control interface 130 of the filter wheel 150, an operator can rotate the filter wheel 150 to bring one of the filters of the wheel 150 to be adjacent to the exit aperture on the target 103 of the x-ray source system 102. In this way, the selected filter (in one example, an air pre-filter) is aligned to filter the beam 104 prior to interaction with the sample 114.

When the sample 114 is exposed to the x-ray beam 104, the x-ray photons transmitted through the sample form an attenuated x-ray beam 106 that is received by the spatially resolved detector system 118. In some other examples, an objective lens such as a zone plate lens is used to form an image onto the detector system 118 of the x-ray imaging system 100. In alternative embodiments the detector system is a flat panel detector.

In the most common configuration of the detector system 118, a magnified projection image of the sample 114 is formed on the detector system 118 with a geometrical magnification that is equal to the inverse ratio of the source-to-sample distance and the source-to-detector distance. Generally, the geometrical magnification provided by the x-ray stage is between 2× and 100×, or more. In this case, the resolution of the x-ray image is limited by the focus spot size or virtual size of the x-ray source system 102.

To achieve high resolution, an embodiment of the x-ray CT system 100 further utilizes a very high resolution detector 124-1 of the detector system 118 in conjunction with positioning the sample 114 close to the x-ray source system 102. In one implementation of the high-resolution detector 124-1, a scintillator is used in conjunction with a microscope objective to provide additional magnification in a range between 2× and 100×, or more.

Other possible detectors can be included as part of the detector system 118 in the illustrated x-ray CT system 100. For example, the detector system 118 can include a lower resolution detector 124-2, as shown in the illustrated embodiment of FIG. 1. This could be a flat panel detector or a detector with a lower magnification microscope objective, in examples. Configurations of one, two, or even more detectors 124 of the detector system 118 are possible.

Preferably, two or more detectors 124-1, 124-2 are mounted on a turret 122 of the detector system 118, so that they can be alternately rotated into the path of the attenuated beam 106 from the sample 114.

Typically, based on operator defined parameters, the controller 210 of the computer system 200 instructs the rotation stage 110 via the control interface 130 to move the sample 114 out of the beam path during x-ray source system 102 calibration. After completion of the calibration portion, the controller 210 moves the sample 114 back into the beam path and rotates the sample 114 relative to the beam 104 in several steps to perform the CT scan of the sample 114 by capturing projects at each angular step.

It should be noted that when acquiring data different systems have differing levels of vibration when moving a sample rapidly. This is not often an issue with normal (rigid) samples, but powders can be jostled during rapid stage movement, inducing sample motion. This is highly system dependent. Note that rapid movement only often occurs at specific points during projection captures for the tomography, particularly when the sample is moved out of the beamline for referencing, or rotated back to 0 degrees to acquire a drift image. The most likely axis to cause significant issues in this regard is the rotation axis, which will return to 0 when taking a sample drift image and referencing (if a non-Y dimension referencing option is chosen). To reduce the likelihood of this occurring, sample drift can be disabled (this will stop rapid rotations to and from 0), or the maximum speed of each axis is reduced.

In one example, the maximum theta rotational speed for the rotation stage 110 is 30 degrees per second. This reduction by 50% to 15 EGU/s has a minimal impact on total acquisition time, but will reduce the amount of sample vibration and potential powder rearrangement (which induces sample motion artefacts in image reconstruction).

In one example, the computer system 200 includes an image processor 202 that analyzes the x-ray projections and possibly performs and accelerates the calculations necessary for tomographic reconstructions created from the x-ray projections. A display device 240, connected to the computer system 200, displays information from the x-ray CT system 100. An input device 250 such as a touch screen, keyboard, and/or computer mouse enables interaction between the operator, the computer system 200, and the display device 240.

A user interface application 208 executes on an operation system 206 that controls access to a central processing unit CPU 205 of the computer system 200. In one example, the operator defines/selects CT scan or calibration parameters via the user interface 208 rendered on the display device 240. These include x-ray acceleration voltage settings, and settings for defining the x-ray energy spectrum of the scan and exposure time on the x-ray source system 102. The operator also typically selects other settings such as the number of x-ray projection images to create for the sample 114, and the angles to rotate the rotation stage 110 for rotating the sample 114 for an x-ray CT scan in the x-ray beam 104, along with the positioning of the sample in the beam along the x, y, and z axes.

Other applications also execute on the CPU 205 of the computer system. In particular, an analytical reconstruction application 209 provides for CT reconstruction algorithms for operating on projections to yield a reconstruction. In addition, a simulation application 207 simulates spectral x-ray emission form the source 102, propagation through the sample geometry, and the resulting spectral response of the detector system 118.

The computer system 200, with the assistance of its image processor 202, accepts the image or projection information from the detector system 118 associated with each rotation angle of the sample 114. The image processor 220 creates a separate projection image for each rotation angle of the sample 114, and combines the projection images using the CT reconstruction algorithms of the analytical reconstruction application 209 executing on the CPU to create 3D tomographic reconstructed volume information for the sample.

X ray microscopy is typically used in non-analytical workflows where the constituent materials within a sample are already well known and expected. This is because the translation of measured attenuation to 3D reconstruction is complex and hard to predict, and dependent on a range of factors including target status, selected filter, sample composition, and scintillator/detector response. In addition, frequently the techniques used to correct for poorly bounded spectral effects on reconstructed attenuation (beam hardening corrections) modulate reconstructed intensity in poorly understood ways. Finally, the absolute value of an x-ray reconstruction is highly dependent on the specific implementation of the typical reconstruction algorithm, such as the Feldkamp-Davis-Kress (FDK) algorithm. The reconstructed intensities can be modulated further by parameters such as pixel size, acquisition geometry, or projection number. For this reason care must be taken in the reconstruction to remove any such arbitrary scaling.

FIG. 2 shows the process for automated segmentation and sample fitting for analytical reconstruction employed by the reconstruction application 209.

In a first step 212, the sample is arranged in the system for a full field of view and the projections are recorded. For each captured projection, it is ensured that at least a portion of the projection corresponds to a passthrough of only air or some other transmission path that modulates the beam in a known fashion with known transmission statistics and is common to all the projections. That is, there is a direct path between the source 102 and the detector 118, such that a portion of the beam 104 entirely misses the sample 114 and that portion of the beam is detected on the detector.

In addition, in the setup, the entirety of the lateral extent of the sample is being imaged in each projection. This ensures that there are no unknown portions of the sample along the path of the projections.

As a consequence, the automated segmentation and sample fitting segments a selected projection into either: 1) sample and air regions or 2) sample, sample holder and air regions (depending on the sample holder used).

In more detail, a histogram is first generated for each row of each projection image in step 214.

Then, in step 215, a central axis estimate is determined for each row. This is accomplished by identifying local minima in the projection histogram evaluated between the 3rd and 99th percentiles of pixel values within the image. A central axis estimate is found on every row in the projection image by finding the centroid of the sample phase.

A central axis is then found by fitting a straight line through all the estimated sample centers in step 216.

The sample region is then identified in step 218 by calculating a distance transform from this central axis and identifying the thresholds of this distance transform which minimize the difference between the thresholder image and the initial segmentation.

The region corresponding to air regions or a known sample holder such as a sample mounting tube is found using a similar approach by fitting it to the tube segmented region in step 220, in one example.

An average intensity profile is then determined by evaluating the image intensities across the air region or sample holder interface (and intensity profile which should be the same between all projections if the sample holder is radially symmetrical, if employed) in step 222.

This intensity profile is then fit against some nominal profile and the projection intensities modified so that every projection has the same intensity values across this profile in step 224.

If an extremely thin sample holder is used (such as when mounting the sample in polyimide film), then the sample holder x-ray interaction is too small that it is not discernible as a distinct region from the histogram. In this case an intensity profile can be used just through the air region—the point is to use a region of known transmission statistics (i.e., air or a known sample holder) to correct every calibration to some nominal distribution.

The projection segmentation routine outlined above also identifies the nominal sample position through all the angles of all the projections. This has the added benefit of allowing an automated volumetric cropping around the sample (the region of interest within the reconstructed volume) to reduce data volumes and data analysis times.

And, once the projections have been corrected for nominal transmission fluctuations, the data is reconstructed using any reconstruction technique available (e.g. FDK) in step 228.

It should be noted that subsequent material and specifically material or mineral identification will depend on the noise level of the reconstructed image, so reconstruction technologies that are less susceptible to reconstruction noise are desirable. One example is filtered back projection that has been denoised with a neural network with minimized intensity shifts.

Spectral variation during sample transmission is a common effect in x-ray imaging of samples using a polychromatic x-ray source. A variety of corrections have been developed for this effect with the side effect of changing nominal transmission values and reconstructed absorption values to pseudo-monochromate them for reconstruction. When indexing the resulting reconstructed tomography, care must be taken to modify the simulated material or mineral absorption using the same algorithm as is used in this reconstruction step, estimating and taking into account the effective energy applied in this pseudo-monochromation. It is also extremely important not to perform any scaling on the reconstructed intensities, for example, such that they fit into some integer range. Therefore, reconstruction as floating point data is important as outlined in step 228.

Once data has been reconstructed, the data must be visualized and specifically presented on the display device 240 of the computer system 200. The data should be presented to the user in a way that identifies each reconstructed material or mineral phase independently. This, however, can be extremely challenging for geological systems, as often phases with noticeably differing attenuation have very different abundances and are distributed in three dimensions so it can be challenging to identify. The data must be visualized statistically in a way that makes each region of independent attenuation contrast apparent.

In addition, reconstructed image intensities may still have some residual variation from scan to scan, which can be corrected by identifying peaks from predefined regions on a multi-dimensional histogram, and scaling the reconstructions such that these peaks occur at the same positions.

In the past, a variety of automated clustering algorithms have been used. In present implementation, however, a peak identification routine is used with peaks identified using a 2D histogram. This technique, first identified by Jones et al., 2007 (A. C. Jones, C. H. Arns, A. P. Sheppard, D. W. Hutmacher, B. K. Milthorpe, and M. A. Knackstedt (2007), Assessment of bone ingrowth into porous biomaterials using MICRO-CT, Imaging Tech. Biomater. Charact., 28(15), 2491-2504).

The data set is plotted on a two dimensional histogram. The X axis of the histograms correspond to the reconstructed effective energy attenuation, corrected by the beam hardening correction algorithm, in units of $mm^{-1}$. The Y axis corresponds to the gradient in this attenuation. Lighter pixels have more 3D voxels in the 2D bin, whereas darker have fewer and the background corresponds to bins with no voxels indexed to them.

While this technique has now largely been superseded by machine learning pixel classification routines, it is still an excellent technique for identifying phases well separated by attenuation and does not suffer from the class imbalance problems common in machine learning segmentation routines. As data is presented statistically it does not require the user to search for rare phases in a large 3D volume. It also allows for specific segmentation settings to be defined relatively easily without the need for extensive training data.

Figures 3A, 3B, 3C:
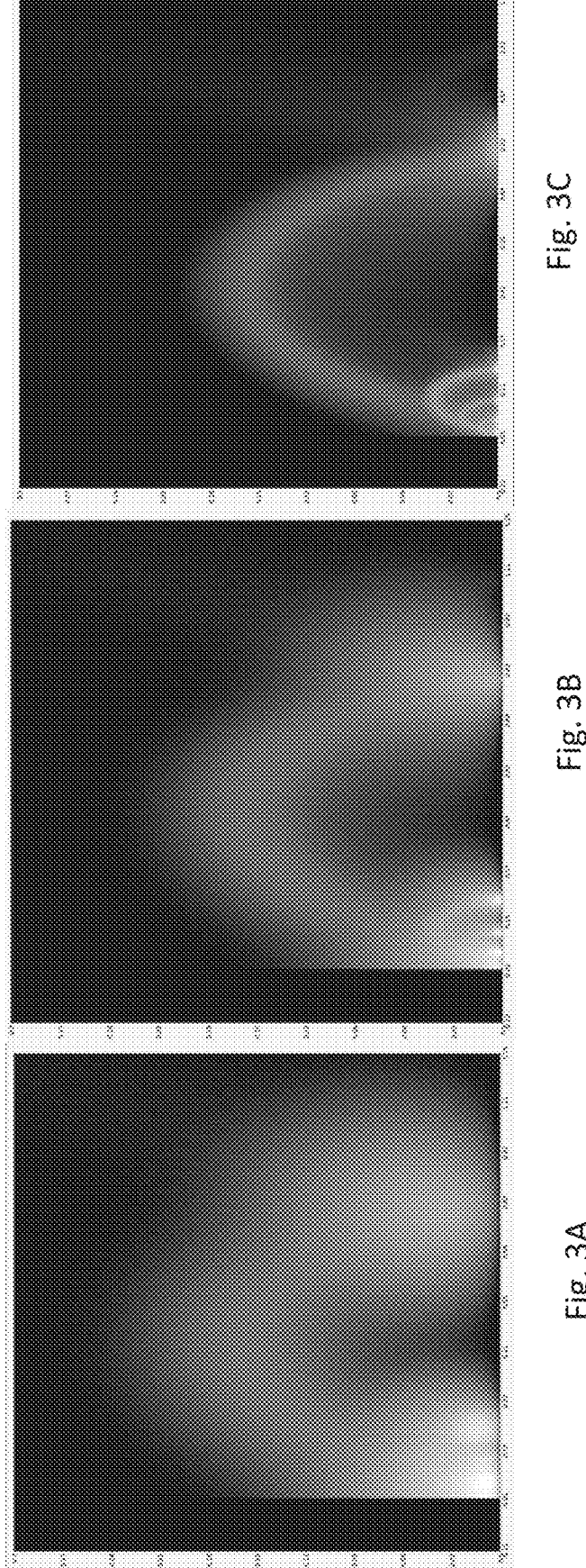

FIGS. 3A, 3B, and 3C are three histograms produced from the same projection data. The pixel brightness corresponds to the number of pixels within that 2D bin.

Regions of low gradient correspond to the centers of large grains or objects and typically are clustered together at the effective reconstructed intensity of their constituent phase.

Regions on the edges of objects suffer from partial volume artifacts, and so have high gradients, and intermediate grayscale intensities between different phases. This causes arcs in the 2D histogram connecting low gradient clusters corresponding to each phase within the image. Note that this clustering will only occur if effective spectral variation across line integrals (i.e. beam hardening) effects are effectively removed from reconstruction. Noise then causes the grayscale values to spread from these clusters, potentially causing overlapping clusters to interfere with each other.

Figure 3D:
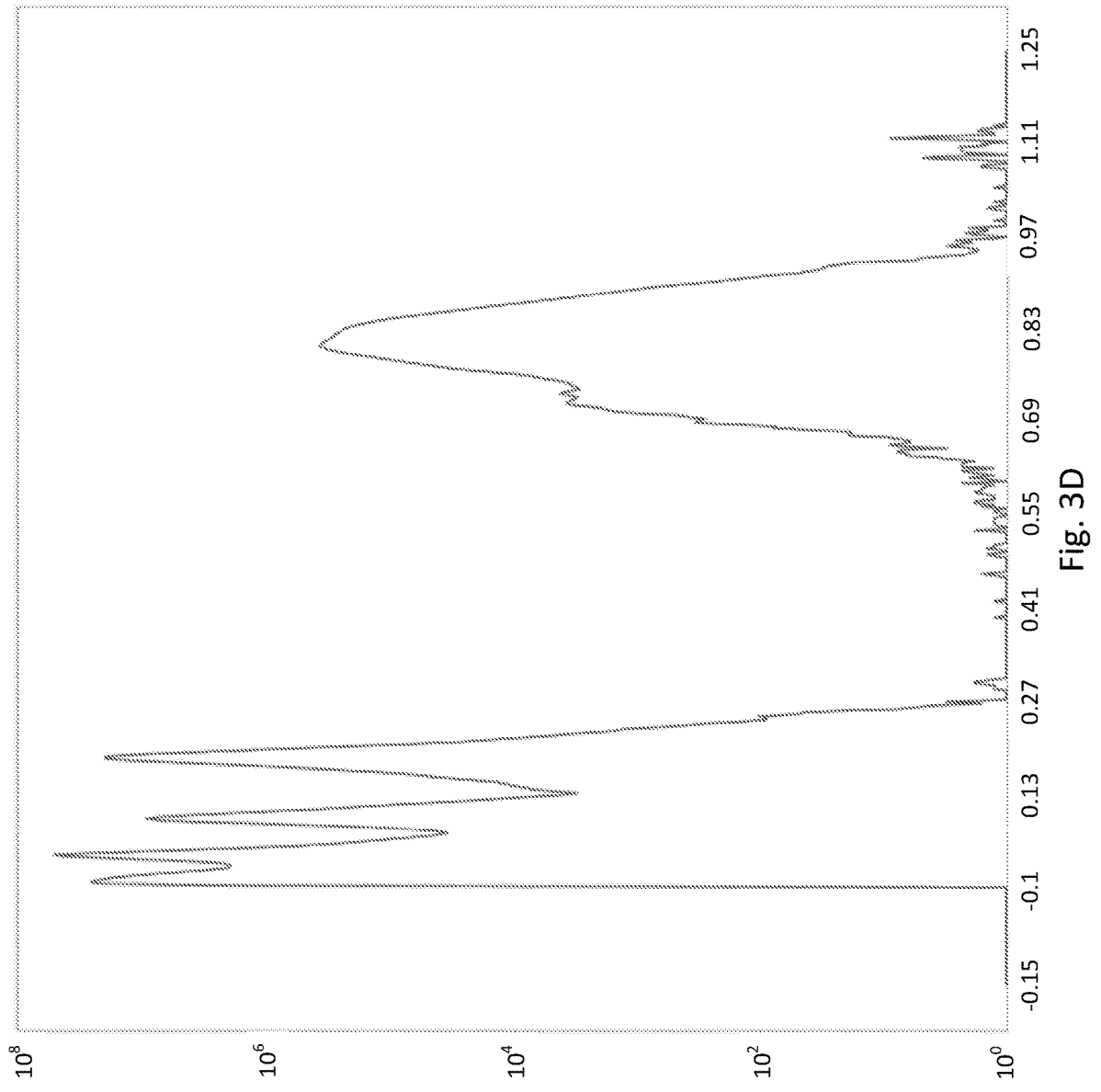
FIG. 3D is a 2D histogram.

Another way of plotting this same data is to look at the line profile corresponding to the lowest gradient regions of this histogram (either the lowest gradient bin, or some average of the lowest gradient bins) shown in FIG. 3D. This produces a low gradient histogram where multiple phases are clearly visible.

This is an extremely useful way of visualizing the data as it allows for clusters of drastically varying abundances to be visualized in the same plot. Note that the data is plotted with a logarithmic Y axis such that the less abundant phases may be many orders of magnitude less abundant than the highly abundant phases.

To identify the phase of each of these peaks it is necessary to perform polychromatic forward x-ray simulations of reconstructed intensity under a variety of different conditions corresponding to the various known sample mounting procedures and system configuration settings (electron gun acceleration voltage, filter settings, detector settings, etc).

Figure 4:
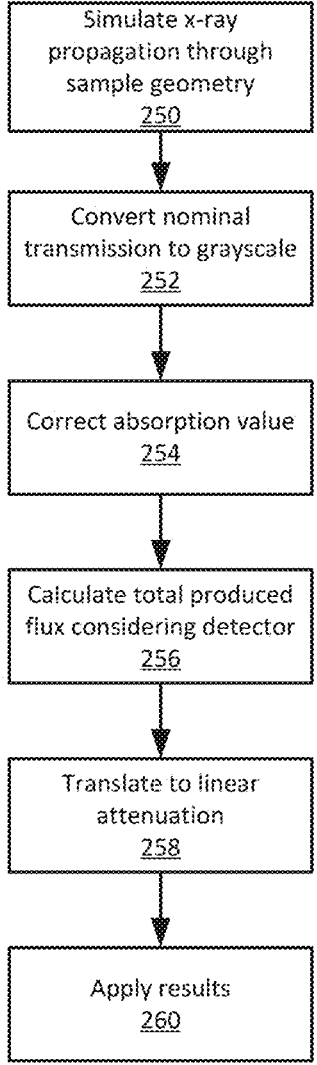
FIG. 4 is a flow diagram showing a process for identifying the phases and reporting in terms of their chemical components.

FIG. 4 is a flow diagram showing a process for identifying the phases. Specifically, the solid phases in the 3D analysis portion are assigned to the mineral compositions. Particle composition and distribution are then reported in terms of their chemical components (assigned to the materials such as minerals/phases identified from the compositional indexing).

In step 250, forward projection algorithms of the simulation application 207 simulate spectral x-ray emission, propagation through the nominal sample geometry, and spectral response of the detector. The simulated light intensity (summed across all energies) measured by the detector is then compared between simulations where an object of known composition, density, and thickness is present within the beam propagation path, and one where it is not. The ratio of these two detected light fluxes corresponds to a nominal transmission of the material object.

In step 252, the nominal transmission of a material object is converted into an effective reconstructed greyscale value by scaling the object absorption (the negative log of its transmission) by its thickness, giving an effective linear attenuation coefficient. Care should be taken to correctly simulate the change in x-ray spectra associated with a small increment of the target material or mineral at the characteristic transmission/attenuation (and spectral shift) within the sample. The characteristic attenuation can be measured directly on the sample data in a range of ways, for example by identifying the sample geometry (as described in FIG. 2) and measuring the average axial transmission through the sample.

This absorption value is then corrected in step 254 using the same beam hardening correction routine used in x-ray reconstruction, and divided by the object thickness used for simulation, to give a linear attenuation coefficient for that object. This value (with units of length) should be linearly proportional to the reconstructed grayscale value of the same material in three dimensional space. This is only the case if the back projection/reconstruction algorithm used normalizes for all system variations which can modify reconstructed attenuation (such as projection number, or system geometry) and has equivalent units of $length^{-1}$. This simulation is preferably a 1D x-ray simulation from emission to detection. Total produced flux is then measured considering detector response.

Figure 5:
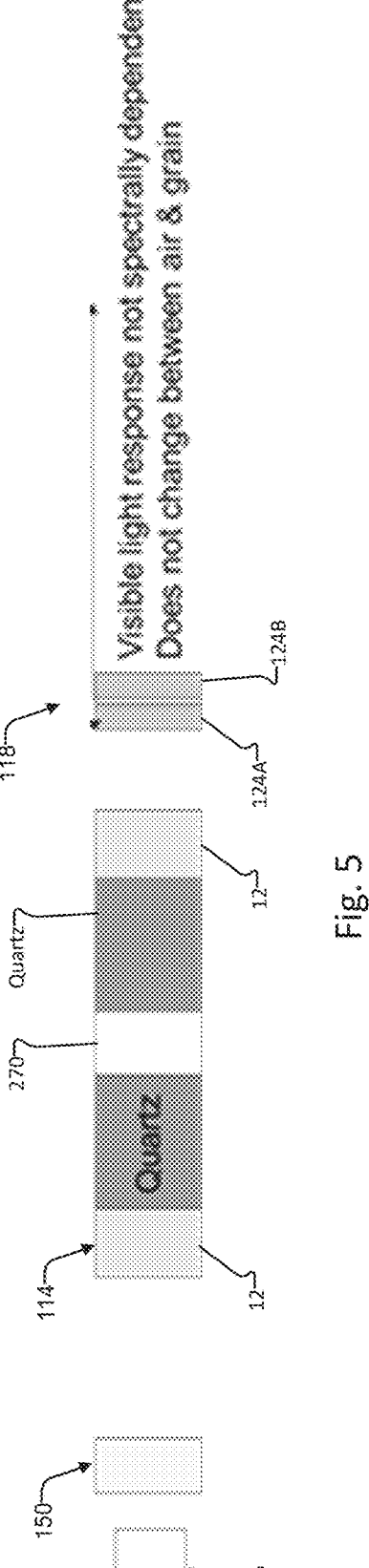
FIG. 5 is a schematic diagram showing a simulation setup.

FIG. 5 shows an exemplary simulation performed by the simulation application 207. X-rays are produced in a tungsten diamond target 102A of the source 102. This simulation is used to yield an accurate forward simulation of the sample and system response.

In more detail, the beam passes through a filter of the filter wheel 150. The beam then enters the sample holder such as tubing 12 and passes through quartz, air, quartz and then exits through the tubing 12 of the sample holder and then is converted in the scintillator 124A to light, which is detected by the optical detector 124B of the selected detector of the detector system 118. The simulation is run where the center spot 270 is air and each of the target material phases that are in, or potentially in, the sample.

Returning to FIG. 4 the total produced flux is measured considering the detector response in step 256 by the simulation application.

Nominal fluxes are calculated for two simulations, one with a sample of transmission equal to the characteristic transmission of the sample+a small mineral grain, and one with only a sample of transmission equal to the characteristic transmission of the sample present. A transmission is calculated, and absorption is then corrected using a beam hardening correction routine. This is then translated into a linear attenuation coefficient by dividing by the material or mineral grain thickness in step 258.

In a specific sample simulation setup shown in FIG. 5, the target material is embedded in quartz. But a range of different setups could be used and give similar results, as long as care is taken to make measured projection attenuation and simulated sample attenuation (and consequent beam hardening effects) approximately similar, and the resulting data treated in the same way by any correction algorithms. A variety of second order effects can further complicate reconstructed grayscale intensities, but these are dealt with by more sophisticated data treatment either on the simulation side or on the imaging side prior to reconstruction.

The simulation results are then applied in step 260. These reconstructed material intensities can then be tabulated and compared to reconstructed intensity clusters in the data 2D histogram described above. Final changes to reconstructed intensity distributions may need to be made, particularly if the simulations performed do not accurately conform to the system imaged. This can induce changes in nominal transmission, presumed spectrum, and subsequent reconstructed image intensities modulated through correction algorithms. Simulated reconstructed intensity can be scaled using linear scaling to best fit measured peak positions.

Figure 6A:
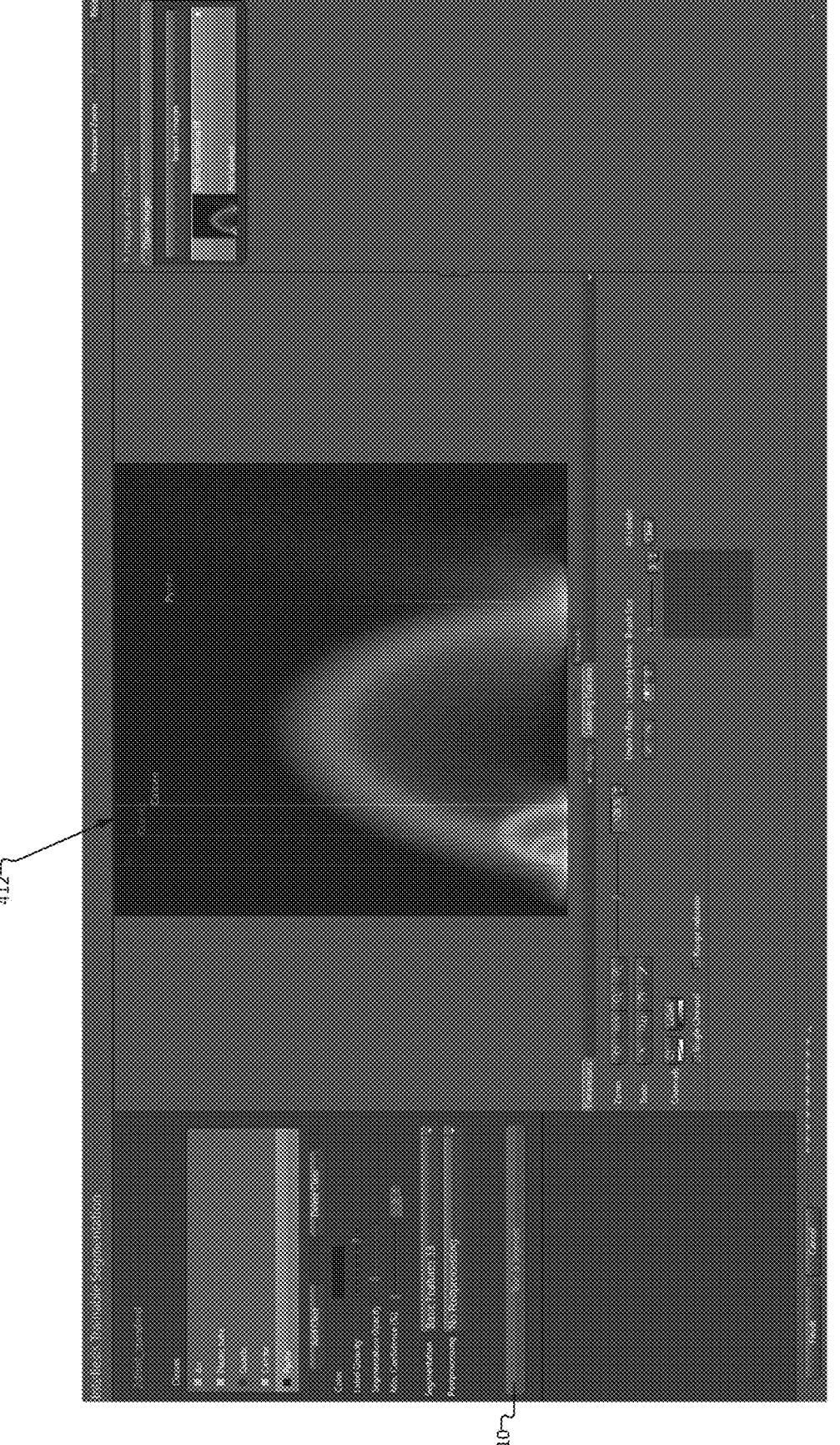
FIGS. 6A-6D show a user interface showing low gradient histograms showing five peaks corresponding to 5 independent phases (from low to high intensity air, plastic tube, quartz, calcite and pyrite) along a logarithmic Y axis.

FIG. 6A shows a low gradient histogram presented in a user interface generated by the user interface application 208 and displayed on the display device 240. It shows the indexed materials using the simulated intensities. It shows five peaks corresponding to 5 independent phases (from low to high intensity air, plastic tube, quartz, calcite and pyrite).

Figure 6B:
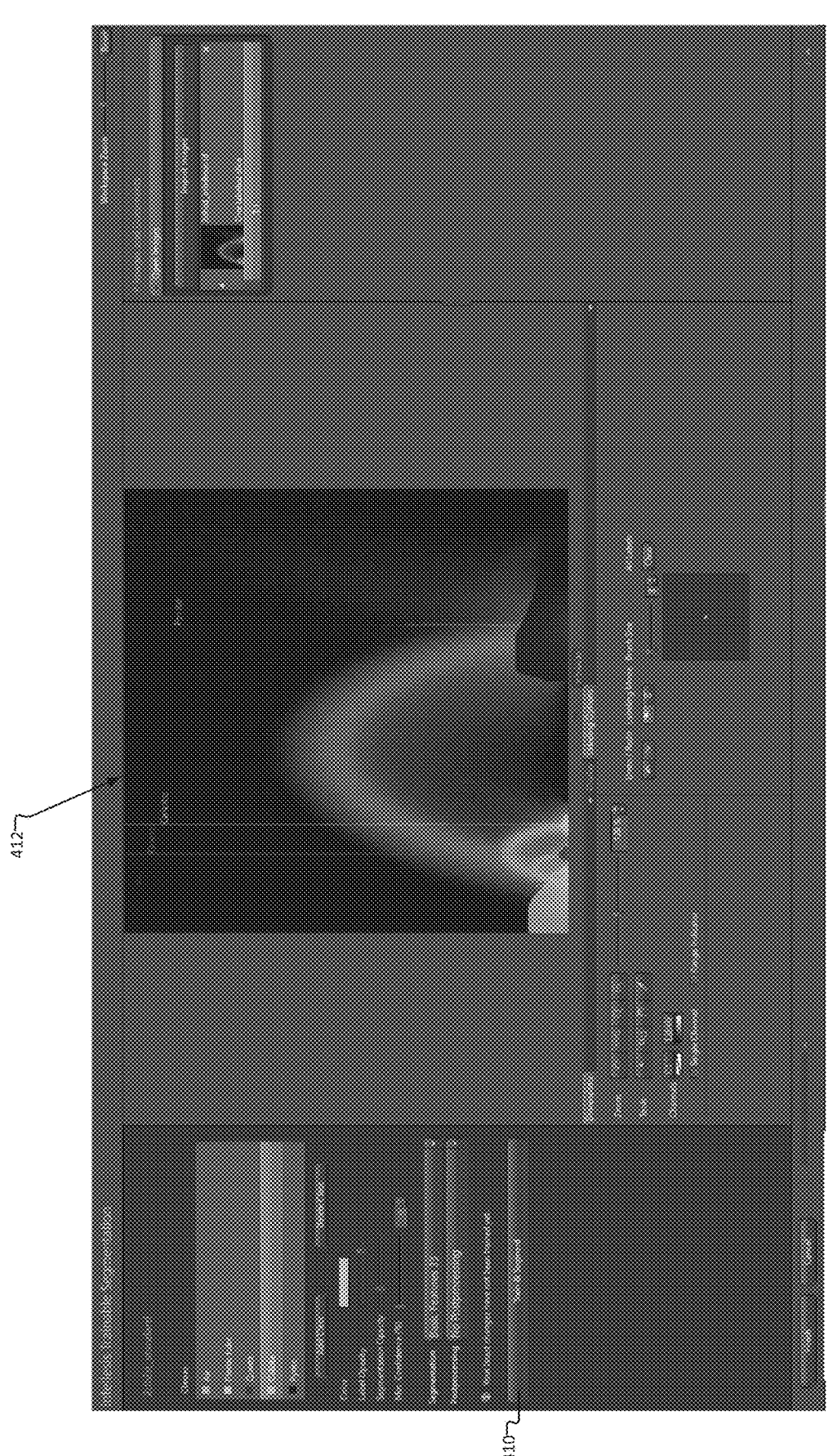

FIG. 6B shows the phase clusters (air, quartz, calcite, and pyrite being labeled.

Note that the pixel labels given for the least and most attenuating phases (in this case air and pyrite respectively) are significantly larger and encompass more bins than those given for intermediate phases, as in this case there are no partial volume artefacts that can interrupt the classification.

Figure 6C:
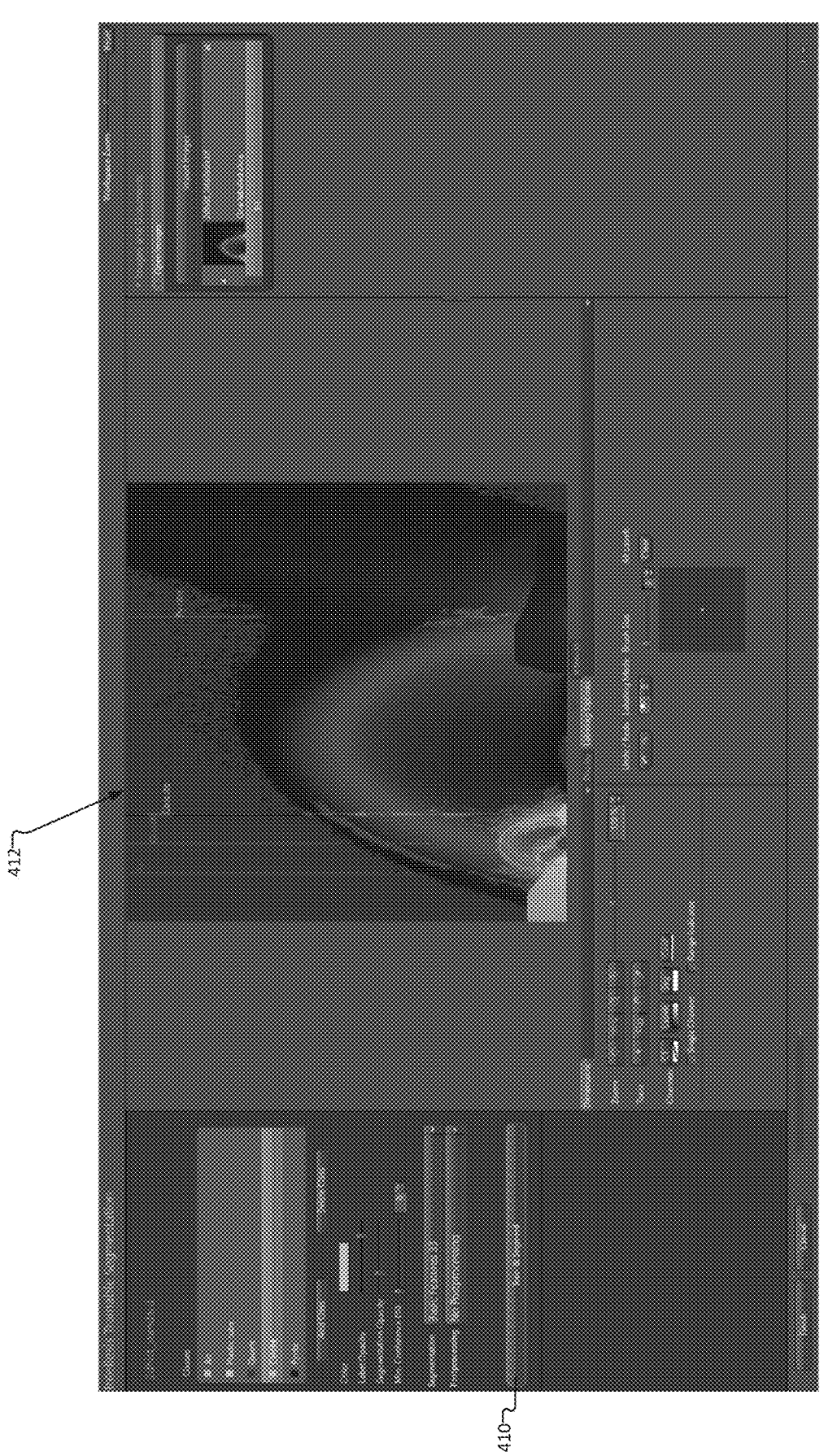

FIG. 6C shows the result produced by selecting the "train and segment" button 410. A "segmentation" now overlays the histogram region 412 of the display screen.

Figure 6D:
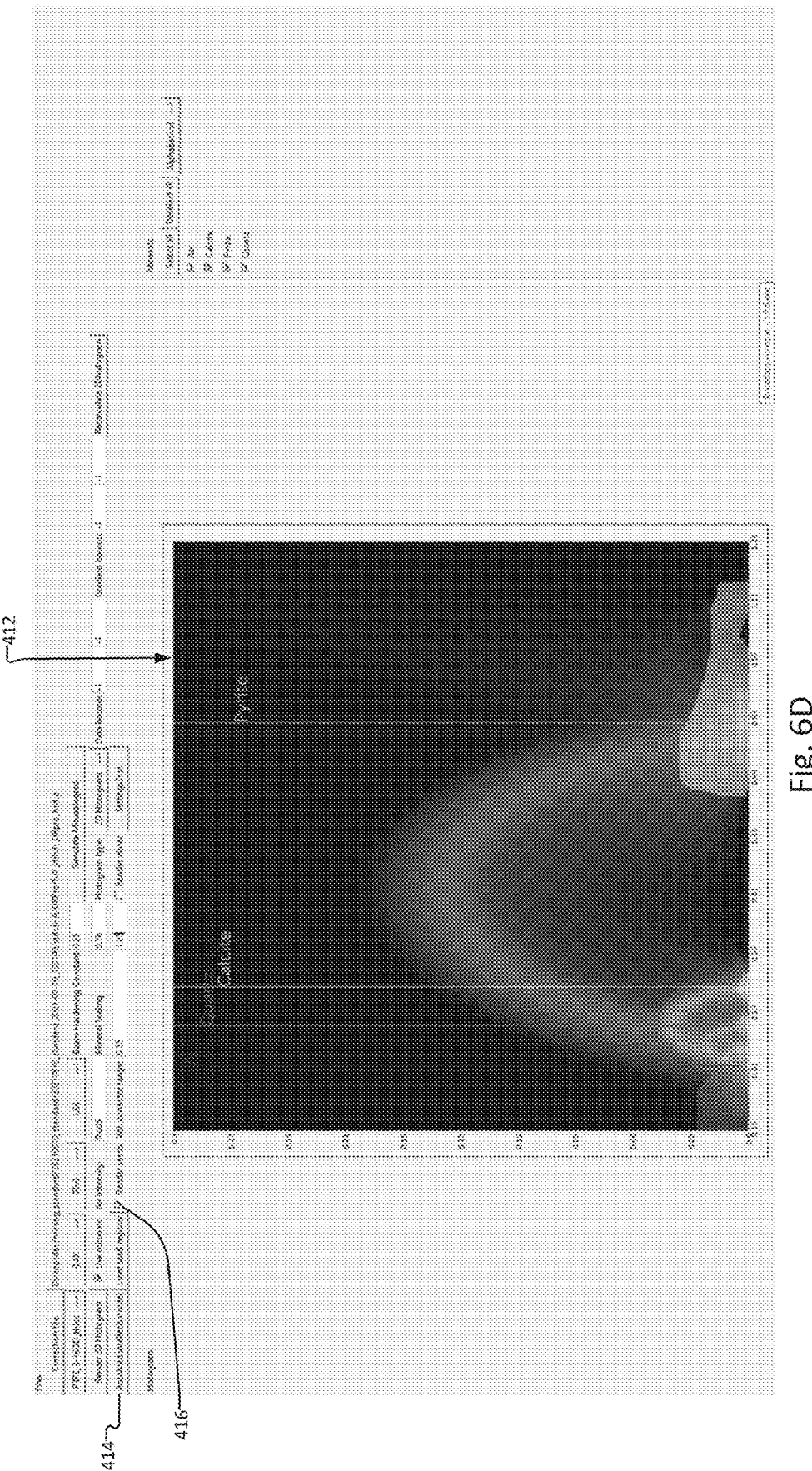

As shown in FIG. 6D, seed region labels are then loaded by selecting the "Auto load intellesis model" button 414. If the labels are correctly loaded the "Render seeds" checkbox 416 will become available and selected. If the histogram is re-rendered as a 2D histogram, the seeds will now appear, as shown.

These 2D histograms are in the segmentation application to define regions of the histogram which correspond to seed regions for a region growing segmentation algorithm that is used to determine the class for each voxel throughout the 3D volume. The regions correspond to multi-dimensional histogram bins to which each pixel in the data set (and subsequent datasets) is indexed. The regions can be grown using any number of region growing algorithms. One implementation uses a watershed transform using the seed regions defined on the 2D histogram as seeds and the grayscale gradient as the watershed landscape.

While this invention has been particularly shown and described with references to preferred embodiments thereof, it will be understood by those skilled in the art that various changes in form and details may be made therein without departing from the scope of the invention encompassed by the appended claims.

What is claimed is:

1. A material characterization method for an x-ray CT system, comprising:
generating one or more volume datasets of samples; and
identifying phases in the samples by correcting the datasets based on simulations, wherein the simulations include assessing when materials of known composition, density, and thickness are present within a beam propagation path, and when they are not to determine a nominal transmission.

2. The method of claim 1, wherein the nominal transmission is converted into an effective reconstructed greyscale value by scaling to give an effective linear attenuation coefficient.

3. The method of claim 1, further including scaling by a beam hardening correction routine.

4. The method of claim 1, wherein the simulations include simulating the x-ray propagation through geometry of the sample.

5. The method of claim 4, wherein the simulations include simulating the response of the x-ray CT system.

6. The method of claim 1, further comprising correcting the projections before being used for generating the volume datasets.

7. The method of claim 6, further comprising correcting the projections as floating point data.

8. The method of claim 1, wherein a passthrough of only air path is in a field of view for projections and is used to generate the one or more volume datasets to create a reference path.

9. An x-ray microscopy CT system, comprising:
a source of generating x-rays;
a sample holder for holding and rotating samples in the beam;
a detector for detecting the beam after interaction with the samples; and
a computer for receiving projections from the detector and generating one or more volume datasets of samples and identifying phases in the samples by correcting the datasets based on simulations, wherein the simulations assess when materials of known composition, density, and thickness are present within a beam propagation path, and when they are not to determine a nominal transmission.

10. The system of claim 9, wherein the nominal transmission is converted into an effective reconstructed greyscale value by scaling to give an effective linear attenuation coefficient.

11. The system of claim 9, wherein the computer further scales by a beam hardening correction routine.

12. The system of claim 9, wherein the computer simulates the x-ray propagation through geometry of the sample.

13. The system claim 12, wherein the simulations include simulating the response of the x-ray CT system.

14. The system of claim 9, wherein the computer corrects the projections before being used for generating the volume datasets.

15. The system of claim 14, wherein the computer correct the projections as floating point data.

16. The method of claim 1, wherein the simulations include comparing simulations of light intensities measured by a detector where the materials of known composition, density, and thickness are present within the beam propagation path, and where the materials of known composition, density, and thickness are not present within the beam propagation path, to determine the nominal transmission.

17. The method of claim 16, wherein a ratio of the light intensities measured by the detector corresponds to the nominal transmission.

18. The method of claim 17, wherein the nominal transmission is used for calibration in correcting the datasets.

* * * * *